United States Patent
Hobart et al.

(10) Patent No.: US 6,770,069 B1
(45) Date of Patent: Aug. 3, 2004

(54) LASER APPLICATOR

(75) Inventors: James L. Hobart, Los Altos, CA (US); Daniel K. Negus, Los Altos, CA (US)

(73) Assignee: Sciton, Inc., Palo Alto, CA (US)

(*) Notice: Subject to any disclaimer, the term of this patent is extended or adjusted under 35 U.S.C. 154(b) by 103 days.

(21) Appl. No.: 10/177,058

(22) Filed: Jun. 21, 2002

Related U.S. Application Data

(60) Provisional application No. 60/300,538, filed on Jun. 22, 2001.

(51) Int. Cl.⁷ .................................................. A61N 5/067
(52) U.S. Cl. ............................. 606/9; 128/898; 606/10
(58) Field of Search ........................... 606/9, 10, 13, 606/16–18; 372/35; 128/898

(56) References Cited

U.S. PATENT DOCUMENTS

| | | | |
|---|---|---|---|
| 2,702,552 A | 2/1955 | Moodie | 128/375 |
| 2,715,315 A | 8/1955 | Giardini | 62/1 |
| 3,307,553 A | 3/1967 | Liebner | 128/400 |
| 3,466,111 A | 9/1969 | Ring | 350/54 |
| 3,538,919 A | 11/1970 | Meyer | 128/398 |
| 3,596,514 A | 8/1971 | Mefferd et al. | 73/190 |
| 3,693,623 A | 9/1972 | Harte et al. | 128/303.1 |
| 3,720,213 A | 3/1973 | Hobart et al. | 128/395 |
| 3,783,407 A | 1/1974 | Mefferd et al. | 331/94.5 C |
| 3,821,510 A | 6/1974 | Muncheryan | 219/121 L |
| 3,834,391 A | 9/1974 | Block | 128/303.1 |
| 3,854,153 A | 12/1974 | Fadler et al. | 5/13 |
| 3,868,592 A | 2/1975 | Yarborough et al. | 331/94.5 C |
| 3,873,941 A | 3/1975 | Yarborough et al. | 331/94.5 L |
| 3,900,034 A | 8/1975 | Katz et al. | 128/395 |
| 3,934,210 A | 1/1976 | Yarborough et al. | 331/94.5 C |
| 3,967,627 A | 7/1976 | Brown | 128/400 |
| 3,973,825 A | 8/1976 | Starkweather | 350/6 |
| 3,995,166 A | 11/1976 | Hobart et al. | 250/566 |
| 4,006,299 A | 2/1977 | Grafton | 358/293 |

(List continued on next page.)

FOREIGN PATENT DOCUMENTS

| | | | |
|---|---|---|---|
| EP | 0 073 617 A1 | 3/1983 | A61C/1/08 |
| EP | 0 164 751 A2 | 12/1985 | H01S/3/097 |
| EP | 0 714 642 A1 | 6/1996 | A61F/2/10 |
| EP | 0 755 698 A2 | 1/1997 | A61N/5/06 |
| EP | 1057454 A2 * | 12/2000 | A61B/18/20 |
| WO | WO 86/02783 | 5/1986 | H01S/3/08 |
| WO | WO 93/03521 | 2/1993 | H01S/3/08 |
| WO | WO 95/15725 | 6/1995 | A61B/17/41 |
| WO | WO 96/34566 | 11/1996 | A61B/17/36 |

OTHER PUBLICATIONS

Brigitte Dreno, MD., et al., "The Benefit of Chilling in Argon–Laser Treatment of Port–Wine Stains," vol. 75, No. 1, Chilling in Argon–Laser Treatment, pp. 42–45.

(List continued on next page.)

*Primary Examiner*—Lee Cohen
*Assistant Examiner*—Henry M. Johnson
(74) *Attorney, Agent, or Firm*—Haverstock & Owens LLP

(57) ABSTRACT

An applicator is configured with an optical window formed from a first and a second lens section. The applicator is configured for modulating the temperature of a working surface while simultaneously exposing the working surface to a radiation source. The first and the second lens sections form boundaries of a medium cavity for channeling a temperature regulating medium which is preferably a cooled liquid medium. The first lens section has an outer lens and an inner lens which are preferably separated by a distance in the range of 0.1 to 1.0 cm and form boundaries of an insulating region. In a preferred method, a temperature regulating medium is circulated through the medium cavity while exposing a target tissue to laser radiation through the optical window. The insulating region helps reduce fogging of the optical window thereby improving visibility through the window and reducing scattering of the laser radiation. Preferably, the insulating region is under vacuum. Alternatively, the insulating region is configured to channel a second temperature regulating medium. The applicator and system of the instant invention are preferably configured for exposing dermis to a pulsed laser source while simultaneously cooling dermis during procedures to remove hair or treat the cutaneous vascular lesions.

44 Claims, 12 Drawing Sheets

U.S. PATENT DOCUMENTS

| | | | |
|---|---|---|---|
| 4,071,031 A | 1/1978 | Lowman | 128/402 |
| 4,122,853 A | 10/1978 | Smith | 128/303.1 |
| 4,140,130 A | 2/1979 | Storm, III | 128/404 |
| 4,143,660 A | 3/1979 | Malyshev et al. | 128/303.1 |
| 4,149,529 A | 4/1979 | Copeland et al. | 128/24.1 |
| 4,150,342 A | 4/1979 | Johnston, Jr. et al. | 331/94.5 S |
| 4,174,154 A | 11/1979 | Kawasaki | 350/299 |
| 4,185,633 A | 1/1980 | Prozorov et al. | 128/303.1 |
| 4,240,431 A | 12/1980 | Komiya | 128/303.1 |
| 4,274,703 A | 6/1981 | Fisli | 350/6.8 |
| 4,276,520 A | 6/1981 | Rosenberg | 331/94.5 P |
| 4,276,779 A | 7/1981 | Davis, Jr. | 73/626 |
| 4,309,998 A | 1/1982 | Aron nee Rosa et al. | 128/303.1 |
| 4,313,093 A | 1/1982 | Suenaga et al. | 331/94.5 D |
| 4,329,997 A | 5/1982 | de Yampert et al. | 128/402 |
| 4,373,816 A | 2/1983 | Laib | 356/375 |
| 4,378,600 A | 3/1983 | Hobart | 372/62 |
| 4,381,007 A | 4/1983 | Doss | 128/303.1 |
| RE31,279 E | 6/1983 | Mefferd et al. | 372/107 |
| 4,388,924 A | 6/1983 | Weissman et al. | 128/303.1 |
| 4,391,275 A | 7/1983 | Fankhauser et al. | 128/303.1 |
| 4,408,602 A | 10/1983 | Nakajima | 128/303.1 |
| 4,461,294 A | 7/1984 | Baron | 128/303.1 |
| 4,473,074 A | 9/1984 | Vassiliadis | 128/303.1 |
| 4,500,996 A | 2/1985 | Sasnett et al. | 372/19 |
| 4,503,854 A | 3/1985 | Jako | 128/303.1 |
| 4,516,564 A | 5/1985 | Koiso et al. | 126/263 |
| 4,538,181 A | 8/1985 | Taylor | 358/208 |
| 4,545,657 A | 10/1985 | Sunago | 350/600 |
| 4,559,942 A | 12/1985 | Eisenberg | 128/303 |
| 4,566,107 A | 1/1986 | Kitaura et al. | 372/38 |
| 4,601,037 A | 7/1986 | McDonald | 372/25 |
| 4,608,978 A | 9/1986 | Rohr | 128/303.1 |
| 4,608,979 A | 9/1986 | Breidenthal et al. | 128/303.1 |
| 4,617,926 A | 10/1986 | Sutton | 128/303.1 |
| 4,660,798 A | 4/1987 | Kinoshita | 248/648 |
| 4,662,730 A | 5/1987 | Outwater et al. | 351/212 |
| 4,665,913 A | 5/1987 | L'Esperance, Jr. | 128/303.1 |
| 4,672,969 A | 6/1987 | Dew | 128/397 |
| 4,684,222 A | 8/1987 | Borrelli et al. | 350/420 |
| 4,733,660 A | 3/1988 | Itzkan | 128/303.1 |
| 4,753,503 A | 6/1988 | Day et al. | 350/3.71 |
| 4,761,047 A | 8/1988 | Mori | 350/96.1 |
| 4,785,456 A | 11/1988 | Kaplan | 372/38 |
| 4,791,927 A | 12/1988 | Menger | 128/303.1 |
| 4,819,669 A | 4/1989 | Politzer | 132/200 |
| 4,852,115 A | 7/1989 | Viherkoski | 372/92 |
| 4,856,513 A | 8/1989 | Muller | 128/303.1 |
| 4,864,578 A | 9/1989 | Proffitt et al. | 372/20 |
| 4,871,252 A | 10/1989 | Beni et al. | 356/347 |
| 4,887,019 A | 12/1989 | Reis et al. | 350/6.1 |
| 4,887,894 A | 12/1989 | Gluzerman et al. | 350/636 |
| 4,896,015 A | 1/1990 | Taboada et al. | 219/121.78 |
| 4,915,484 A | 4/1990 | Yamamoto | 350/420 |
| 4,939,739 A | 7/1990 | Hobart et al. | 372/107 |
| 4,941,093 A | 7/1990 | Marshall et al. | 364/413.01 |
| 4,949,358 A | 8/1990 | Kantorski et al. | 372/94 |
| 4,963,143 A | 10/1990 | Pinnow | 604/14 |
| 4,971,411 A | 11/1990 | Takanashi | 350/6.5 |
| 5,000,752 A | 3/1991 | Hoskin et al. | 606/9 |
| 5,023,886 A | 6/1991 | Hobart et al. | 372/99 |
| 5,033,061 A | 7/1991 | Hobart et al. | 372/107 |
| 5,046,184 A | 9/1991 | Chee et al. | 372/18 |
| 5,052,017 A | 9/1991 | Hobart et al. | 372/99 |
| 5,055,048 A | 10/1991 | Vassiliadis et al. | 433/215 |
| 5,057,104 A | 10/1991 | Chess | 606/9 |
| 5,059,192 A | 10/1991 | Zaias | 606/9 |
| 5,061,062 A | 10/1991 | Schneiter | 356/1 |
| 5,098,426 A | 3/1992 | Sklar et al. | 606/5 |
| 5,123,028 A | 6/1992 | Hobart et al. | 372/95 |
| 5,123,845 A | 6/1992 | Vassiliadis et al. | 433/215 |
| 5,125,922 A | 6/1992 | Dwyer et al. | 606/3 |
| 5,125,923 A | 6/1992 | Tanner et al. | 606/10 |
| 5,128,509 A | 7/1992 | Black et al. | 219/121.76 |
| 5,140,606 A | 8/1992 | Yarborough et al. | 372/64 |
| 5,152,759 A | 10/1992 | Parel et al. | 606/5 |
| 5,168,386 A | 12/1992 | Galbraith | 359/215 |
| 5,182,857 A | 2/1993 | Simon | 30/34.05 |
| 5,190,032 A | 3/1993 | Zacoi | 128/400 |
| 5,198,926 A | 3/1993 | Sheinis et al. | 359/356 |
| 5,207,576 A | 5/1993 | Vassiliadis et al. | 433/215 |
| 5,210,398 A | 5/1993 | Metlitsky | 235/462 |
| 5,226,907 A | 7/1993 | Tankovich | 606/133 |
| 5,227,910 A | 7/1993 | Khattak | 359/211 |
| 5,269,778 A | 12/1993 | Rink et al. | 606/12 |
| 5,275,564 A | 1/1994 | Vassiliadis et al. | 433/226 |
| 5,282,797 A | 2/1994 | Chess | 606/9 |
| 5,292,320 A | 3/1994 | Brown et al. | 606/15 |
| 5,300,066 A | 4/1994 | Manoukian et al. | 606/15 |
| 5,312,398 A | 5/1994 | Hobart et al. | 606/14 |
| 5,335,242 A | 8/1994 | Hobart et al. | 372/95 |
| 5,344,418 A | 9/1994 | Ghaffari | 606/9 |
| 5,359,669 A | 10/1994 | Shanley et al. | 382/6 |
| 5,360,447 A | 11/1994 | Koop | 623/15 |
| 5,375,132 A | 12/1994 | Connors et al. | 372/34 |
| 5,405,368 A | 4/1995 | Eckhouse | 607/88 |
| 5,411,502 A | 5/1995 | Zair | 606/10 |
| 5,413,555 A | 5/1995 | McMahan | 606/4 |
| 5,421,819 A | 6/1995 | Edwards et al. | 604/22 |
| 5,423,801 A | 6/1995 | Marshall et al. | 606/5 |
| 5,425,727 A | 6/1995 | Koziol | 606/5 |
| 5,425,728 A | 6/1995 | Tanovich | 606/9 |
| 5,426,662 A | 6/1995 | Mefferd et al. | 372/99 |
| 5,464,013 A | 11/1995 | Lemelson | 128/653.1 |
| 5,474,549 A | 12/1995 | Ortiz et al. | 606/9 |
| 5,480,396 A | 1/1996 | Simon et al. | 606/4 |
| 5,486,172 A | 1/1996 | Chess | 606/20 |
| 5,520,679 A | 5/1996 | Lin | 606/5 |
| 5,522,813 A | 6/1996 | Trelles | 606/2 |
| 5,531,470 A | 7/1996 | Townsend | 280/730.2 |
| 5,531,740 A | 7/1996 | Black | 606/9 |
| 5,540,676 A | 7/1996 | Freiberg | 606/3 |
| 5,546,214 A | 8/1996 | Black et al. | 359/203 |
| 5,582,752 A | 12/1996 | Zair | 219/121.85 |
| 5,585,698 A | 12/1996 | Langhans et al. | 315/200 A |
| 5,595,568 A | 1/1997 | Anderson et al. | 606/9 |
| 5,611,795 A | 3/1997 | Slatkine et al. | 606/9 |
| 5,618,285 A | 4/1997 | Zair | 606/10 |
| 5,620,435 A | 4/1997 | Belkin et al. | 606/4 |
| 5,620,478 A | 4/1997 | Eckhouse | 607/88 |
| 5,624,437 A | 4/1997 | Freeman et al. | 606/12 |
| 5,626,631 A | 5/1997 | Eckhouse | 607/88 |
| 5,637,850 A | 6/1997 | Honda | 235/454 |
| 5,642,287 A | 6/1997 | Sotiropoulos et al. | 364/474.08 |
| 5,643,334 A | 7/1997 | Echhouse et al. | 607/88 |
| 5,645,550 A | 7/1997 | Hohla | 606/108 |
| 5,651,784 A | 7/1997 | Klopotek | 606/5 |
| 5,655,547 A | 8/1997 | Karni | 128/898 |
| 5,659,563 A | 8/1997 | Reed et al. | 372/101 |
| 5,662,643 A | 9/1997 | Kung et al. | 606/3 |
| 5,662,644 A | 9/1997 | Swor | 606/9 |
| 5,735,844 A | 4/1998 | Anderson et al. | 606/9 |
| 5,738,677 A | 4/1998 | Colvard et al. | 606/4 |
| 5,756,981 A | 5/1998 | Roustaei et al. | 235/462 |
| 5,769,787 A | 6/1998 | Lemelson | 600/407 |
| 5,770,847 A | 6/1998 | Olmstead | 235/462 |
| 5,781,574 A * | 7/1998 | Connors et al. | 372/35 |
| 5,782,822 A | 7/1998 | Telfair et al. | 606/5 |
| 5,783,798 A | 7/1998 | Abraham | 219/121.73 |
| 5,814,803 A | 9/1998 | Olmstead et al. | 235/462 |

| | | | |
|---|---|---|---|
| 5,814,827 A | 9/1998 | Katz | 250/556 |
| 5,846,080 A | 12/1998 | Schneider | 433/215 |
| 5,849,006 A | 12/1998 | Frey et al. | 606/5 |
| 5,865,830 A | 2/1999 | Parel et al. | 606/5 |
| 5,868,731 A | 2/1999 | Budnik et al. | 606/9 |
| 5,883,658 A | 3/1999 | Schubert et al. | 347/258 |
| 5,900,963 A | 5/1999 | Li et al. | 359/205 |
| 5,931,848 A | 8/1999 | Saadat | 606/167 |
| 5,933,268 A | 8/1999 | Li et al. | 359/207 |
| 5,938,657 A | 8/1999 | Assa et al. | 606/9 |
| 5,941,893 A | 8/1999 | Saadat | 606/180 |
| 5,984,915 A | 11/1999 | Loeb et al. | 606/9 |
| 5,997,531 A | 12/1999 | Loeb et al. | 606/13 |
| 6,066,127 A | 5/2000 | Abe | 606/2 |
| RE36,872 E | 9/2000 | Zair | 606/10 |
| 6,162,213 A | 12/2000 | Stewart | 606/10 |
| 6,228,075 B1 | 5/2001 | Furumoto | 606/9 |
| 6,228,076 B1 | 5/2001 | Winston et al. | 606/11 |
| 6,267,771 B1 | 7/2001 | Tankovich et al. | 606/131 |
| 6,270,222 B1 * | 8/2001 | Herpst | 359/511 |
| 6,471,691 B1 | 10/2002 | Kobayashi et al. | 606/4 |
| 6,524,330 B1 | 2/2003 | Khoobehi et al. | 607/89 |
| 6,613,042 B1 | 9/2003 | Tankovich et al. | 606/10 |
| 2001/0007068 A1 * | 7/2001 | Ota et al. | 606/9 |
| 2001/0029364 A1 * | 10/2001 | Almeida | 606/9 |
| 2003/0032949 A1 | 2/2003 | Schuele et al. | 606/4 |
| 2003/0078567 A1 | 4/2003 | Dorin et al. | 606/4 |

OTHER PUBLICATIONS

Barbara A. Gilchrest.et al., "Chilling Port Wine Stains Improves the Response to Argon Laser Therapy," Plastic and Reconstructive Surgery, vol. 69, No. 2, 1982, pp. 278–283.

Akira Yanai, M.D., et al., "Argon Laser Therapy of Port–Wine Stains: Effects and Limitations," vol. 75, No. 4, Apr. 1985, pp. 520–525.

R. Rox Anderson et al., "Selective Photothermolysis: Precise Microsurgery by Selective Absorption of Pulsed Radiation," vol. 220, Apr. 1983, pp. 524–527.

Rory C.D. Herdman et al., "An in vitro comparison of the Erbium: YAG laser and the carbon dioxide laser in laryngeal surgery," vol. 107, Oct. 1993, pp. 908–911.

Joseph T. Walsh, Jr. et al., "Pulsed CO2 Laser Tissue Ablation: Measurement of the Ablation Rate," Laser in Surgery and Medicine, 1998, pp. 264–275.

Joseph T. Walsh, Jr. et al., "Effect of Tissue Type and Pulse Duration on Thermal Damage," 1998 Alan R. Liss, Inc., pp. 110–118.

Joseph T. Walsh, Jr. et al., "Pulsed CO2 Laser Ablation of Tissue: Effect of Mechanical Properties," Transactions on Biomedical Engineering, vol. 36, No. 12, Dec. 1989, pp. 1195–1201.

E. Victor Ross, MD., et al., "Effects of Heterogeneous Absorption of Laser Radiation in Biotissue Ablation: Characterization of Ablation of Fat with a Pulsed CO2 Laser," Laser in Surgery and Medicine, 1997, pp. 59–64.

"Erbium Laser Gaining Popularity for Cosmetic Applications", Medical Laser Report, Nov. 1996, pp. 2–3.

U. Hohenleutner et al., "Fast and Effective Skin Ablation with an Er:YAG Laser: Determination of Ablation Rates and Thermal Damages Zones," Laser in Surgery and Medicine 20, 1997, pp. 242–247.

Brigita Drnovsek–Olup et al., "Use of Er:YAG Laser for Benign Skin Disorders," Laser in Surgery and Medicine 21, 1997, pp. 13–19.

Leon Goldman, MD., et al., "Replica Microscopy and Scanning Electron Microscopy of Laser Impacts on the Skin," The Journal of Investigative Dermatology, vol. 52, No. 1, pp. 18–24.

Melanie C. Grossman M.D., et al., "Damage to hair follicles by normal–mode ruby laser pulses," Journal of the American Academy of Dermatology, Dec. 1996, pp. 889–894.

Luigi L. Polla MD., et al., "Melanosomes Are a Primary Target of Q–Switched Ruby Laser Irradiation in Guinea Pig Skin," The Society for Investigation Dermatology, Inc., vol. 89, No. 3, 1987, pp. 281–286.

"The Journal of Investigative Dermatology," Apr. 1987, vol. 88, No. 4, pp. 523.

N. Douglas Gossman, MD., et al., "Prospective Evaluation of the Argon Laser in the Treatment of Trichiasis," Mar. 1992, vol. 23, No. 3, 183–187.

"Selective Photothermolysis: Precise Microsurgery by Selective Absorption of Pulsed Radiation," Science, vol. 220, Apr. 1983, pp. 524–527.

R. Rox Anderson et al., "The Optics of Human Skin," The Journal of Investigative Dermatology 77, 1981, pp. 13–19.

Leon Goldman M.D., et al., "Treatment of Basal Cell Epithelioma by Laser Radiation," Epithelioma–Goldman & Wilson, 1961, vol. 189, No. 10, pp. 773–775.

Leon Goldman MD., et al., "Laser Action at the Cellular Level," Multidiscipline Research Forum, JAMA, Nov. 7, 1996, vol. 198, No. 6, pp. 641–644.

Leon Goldman MD., et al., "Biomedical Aspects of Lasers" JAMA, Apr. 20, 1964, vol. 188, No. 3, pp. 302–306.

Leon Goldman MD., et al., "Effect of the Laser Beam on the Skin," Preliminary Report, 2 pgs.

Leon Goldman MD., et al., "Effect of the Laser Beam on the Skin," III. Exposure of Cytological Preparations, pp. 247–251.

"Pathology of the Effect of the Laser Beam on the Skin," Nature, Mar. 2, 1963, vol. 197, pp. 912–914.

"Preliminary Investigation of Fat Embolization from Pulsed Ruby Laser Impacts of Bone," Nature, vol. 221, Jan. 1969, pp. 361–363.

Leon Goldman MD., et al., "Radiation from a Q–Switched Ruby Laser: Effect of Repeated Impacts of Power Output of 10 Megawatts on a Tattoo of Man," pp. 69–71.

Roland Kaufmann MD., et al., "Pulsed Er:YAG– and 308 nm UV–Excimer Laser: An In Vitro and In Vivo Study of Skin–Ablative Effects," Laser in Surgery and Medicine 9, 1989, pp. 132–140.

A.D. Zweig et al., "A Comparative Study of Laser Tissue Interaction of 2.94 $\mu$m and 10.6$\mu$m," Appl. Phys. B 47, 1998, pp. 259–265.

B.R. Burkhardt MD., et al., "Are More Passes Better? Safety versus Efficacy with Pulsed CO2 Laser," Cosmetic, Nov. 1997, pp. 1531–1534.

Roland Kaufmann MD., et al., "Cutting and Skin–Ablative Properties of Pulsed Mid–Infrared Laser Surgery," 1994, pp. 112–118.

Joseph T. Walsh, Jr. MD., et al., "Er:YAG Laser Ablation of Tissue: Measurement of Ablation Rate," Laser in Surgery and Medicine 9, 1989, pp. 327–337.

Joseph T. Walsh, Jr., MD., et al., "Er:YAG Laer Ablation of Tissue: Effect of Pulse Duration and Tissue Type on Thermal Damage," Laser in Surgery and Medicine p, 1989, pp. 314–326.

Roland Kaufmann MD., "Pulsed 2.94–$\mu$m erbium–YAG Laser Skin Ablation Experimental Results and First Clinical Application," 1990, 15, pp. 389–393.

Raimund Hibst et al., Effects of Laser Parameters on Pulsed Er–YAG Laser Skin Ablation<Lasers in Medical Science, vol. 6:9391, 1991, pp. 391–397.

* cited by examiner

LASER APPLICATOR

RELATED APPLICATIONS

This Patent Application claims priority under 35 U.S.C. 119 (e) of the co-pending U.S. Provisional Patent Application, Serial No. 60/300,538, filed Jun. 22, 2001, and entitled "LASER APPLICATOR". The Provisional Patent Application, Serial No. 60/300,538, filed Jun. 22, 2001, and entitled "LASER APPLICATOR" is also hereby incorporated by reference.

FIELD OF THE INVENTION

The present invention relates to devices and systems for modulating the temperature of a working surface. More specifically, this invention relates to a device and a system for modulating the temperature of a working surface while exposing the working surface to radiation.

BACKGROUND OF THE INVENTION

Lasers are known to have numerous medical applications. For example, lasers are used to ablate and cauterize tissue. Lasers are also used in a variety of therapeutic dermal procedures including removal of unwanted hair and treatment of Port Wine Stains or cutaneous vascular lesions. Some of the earliest attempts to develop therapeutic dermal procedures using lasers are described by Solomon and Goldman in "Histopathology of Laser Treatment of Port Wine Lesions: Biopsy Studies of Treated Area up to Three Years After Laser Impacts", published in *The Journal of Investigative Dermatology* 50, 141, 1968.

During the early stages of developing these therapeutic dermal procedures there was speculation regarding the transient modification of the skin prior to treatment with the laser source. Gilchrest et al. teach cooling the epidermis prior to treatment of Port Wine Stains with an argon laser in "Chilling Port Wine Stains Improves Response to Argon Laser Therapy" published in *Plastic and Reconstructive Surgery* 69, 2, 1982. Gilchrest et al. states that Port Wine Stains are more violaceous (pinkish red) when cooled and thus exhibit improved absorption of the laser radiation. In "Argon Laser Therapy of Port-Wine Stains: Effects and Limitations" published in *Plastic and Reconstructive Surgery*, 75 (4) 1985, Yanai et al. reported one of the first attempts to treat dermis with a laser source while simultaneously cooling. Yanai et al. used an admixture of cold water and ice circulated through an apparatus formed from two acrylic plates. The apparatus was placed on the target tissue and the laser therapy was conducted through the apparatus. The results of Yanai et al. were not statistically convincing of the benefits of cooling dermis during exposure to a laser source. Never-the-less further studies have been convincing regarding the benefits of cooling dermis during laser treatment and today cooling dermis while exposing the dermis to a laser source is a preferred method for both hair removal, vascular lesions and malformations and the treatment of Port Wine Stains.

A cooling apparatus and method for removing hair is described in U.S. Pat. Nos. 5,735,844 and 5,595,568, both issued to Anderson et al. A cooling apparatus and method for targeting cutaneous vascular lesions is described in U.S. Pat. Nos. 5,057,104 and 5,282,797, both issued to Chess. The cooling devices described within these patents have a propensity to develop or collect condensation on the optical window of the cooling device during laser treatment. The condensation or "fogging" not only obstructs the physician's view of the tissue, but also scatters the laser light leading to incomplete or inconsistent treatment of the target dermis. Because of the fogging, some physicians apply a wax or ointment to the optical window of the cooling device to reduce the condensation. However, waxes and ointments wear off or streak the optical window and again reduce the physician's visibility of the target tissue and increase laser scatter.

SUMMARY OF THE INVENTION

The apparatus of the current invention is configured for modulating the temperature of a working surface while simultaneously exposing the working surface with a radiation source. The apparatus has lens sections which form an optical window that is transparent to the radiation being used. The lens sections are formed from any suitable transparent material, but preferably include at least one formed from sapphire. The apparatus of the instant invention preferably is configured for regulating the temperature of a target tissue while the target tissue is simultaneously being exposed to a laser source. The apparatus, also referred to herein as an applicator, is preferably used in procedures to remove hair or to treat cutaneous vascular lesions or other dermal malformations.

The applicator has a first lens section and a second lens section. The first lens section has an outer lens and an inner lens. The outer lens and the inner lens are preferably spaced apart by an average distance of 0.1 to 1.0 cm to form an insulating region between the outer lens and the inner lens. The second lens section is preferably positioned coincident to the first lens section such that the first lens section and the second lens section form the optical window. The optical surface area of the first and the second lens sections are preferably matched or, alternatively, are different. Further, the lens sections are flat or shaped to focus or modulate the radiation being used. Preferably, the optical surface area of the second lens section is in a range of 1.0 to 50 cm² and has a shape that is suitable for use in medical laser procedures, such as curved or flat.

The first and the second lens sections form the boundaries of a medium cavity configured to channel a temperature modulating medium. The first and the second lens sections are preferably secured together by a frame section which secures the first and the second lens sections in a position, whereby the first and the second lens sections are separated by an average distance between 0.05 to 0.5 cm. The frame section has a first and a second aperture through which the temperature modulating medium enters and exits the medium cavity. At least one of the first and second apertures is preferably fenestrated to control the flow of the temperature modulating medium through the medium cavity. The first aperture is coupled to an inlet section and the second aperture is coupled to an outlet section each configured to be coupled to a corresponding outlet and inlet of a circulating mechanism. The circulating mechanism urges the temperature regulating medium through the medium cavity and preferably controls the temperature of the medium.

According to a preferred embodiment of the invention the insulating region is under vacuum. Accordingly, the outer lens and the inner lens of the first lens section form a thermo-pane structure. Alternatively, the insulating region may contain an insulating gas, such as dry nitrogen or air. Alternatively, the insulating region is configured with a second inlet and a second outlet, wherein a second temperature modulating medium is channeled through the insulating region.

The applicator is a hand-held applicator configured to be controlled independently from a laser source, wherein a handle section secures to the frame section at a preferred angle relative to the optical window. Alternatively, the handle section is hingably coupled to the frame section, such that the optical window can assume a range of angles relative to the handle section. In further embodiments, the inlet and outlet sections are integral with the handle section and pass through the handle section to couple to the circulating mechanism.

In the system of the instant invention, the applicator is coupled to a laser source or optics for delivering the radiation from the laser source to the target tissue. Accordingly, the system includes a bracket section for coupling the applicator to a laser housing structure. Preferably, the bracket secures the applicator in a position which allows the laser to pass directly through the optical window of the applicator. The applicator is coupled to the laser housing by any number of bracket designs, but is preferably coupled through the inlet and outlet sections, whereby the bracket attaches to the inlet and outlet sections.

In an alternate system of the instant invention, the system has an optical configuration for delivering radiation from a radiation source to a target tissue. The optical configuration includes an applicator coupled to a radiation source or suitable optics for delivering the radiation to the target tissue. Suitable optics include, but are not limited to, focusing lens, mirrors and optical fibers. Preferably, the radiation source is a laser source with a wavelength in the range of 400 to 11,000 nm. More preferably, the laser source is a pulsed laser source configured to generate a predetermined pulsed sequence during procedures for removing hair or for treating cutaneous vascular lesions.

In use the epidermis of the target tissue is exposed to the predetermined sequence of laser pulses through the transparent window of the applicator. A temperature modulating medium is channeled through the medium cavity and through the inlet and outlet sections. In the preferred method of the instant invention, the medium is cooled and removes heat from the target tissue.

As mentioned, the bottom lens section is flat or contoured depending on the desired focusing properties of the window and/or the morphology of the target tissue being treated. The outer surface of the bottom lens section is placed in contact with the epidermis of the target tissue during the laser exposure. Alternatively, a dye, a gel, an oil or other suitable contact medium is placed between the epidermis and the outer surface of the second lens section to facilitate the transfer of radiation to the tissue, the transfer of heat to the applicator and/or to reduce friction between the applicator and tissue when pressure is applied.

The temperature modulating medium is preferably a cooled liquid medium, such as a mixture of approximately 50% water and 50% ethylene glycol. The cooled liquid medium is circulated through the medium cavity by a circulation mechanism with a pump unit and a refrigerator unit. The refrigerator unit preferably cools the liquid medium to temperatures between −10 to +10 degrees centigrade before recirculating the liquid medium through the medium cavity of the applicator.

During treatment of the target tissue, the insulating region helps to modulate or regulate the temperature of the outer surface of the first lens section. Accordingly, while cooling the target tissue, the insulating region helps to prevent the transfer of heat from the outer lens of the first lens section to the cooling medium and, thereby, reduces fogging on the outer surface of the first lens section.

The insulating region is preferably a vacuum insulating region or a dry gas. Alternatively, the insulating region is configured with an inlet and an outlet to channel a second temperature modulating medium, whereby the second temperature modulating medium modulates the temperature of the outer lens of the first lens section.

BRIEF DESCRIPTION OF THE DRAWINGS

FIG. 8b shows a fenestrated inlet or outlet section used in the hand-held applicator shown in FIG. 8a.

FIG. 8c shows a schematic cross-sectional view of the optical window of the applicator shown in FIG. 8a.

DETAILED DESCRIPTION OF A PREFERRED EMBODIMENT

Figure 1A:
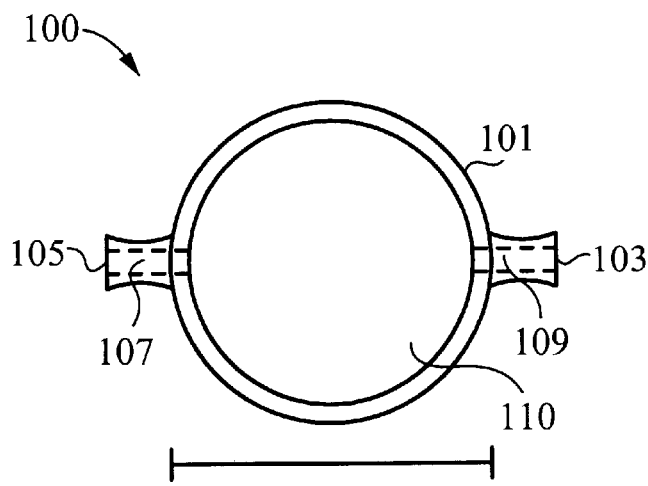
FIGS. 1a–b illustrate a top and a side view of an optical window portion of an applicator for modulating the temperature of a working surface.
Figure 1B:
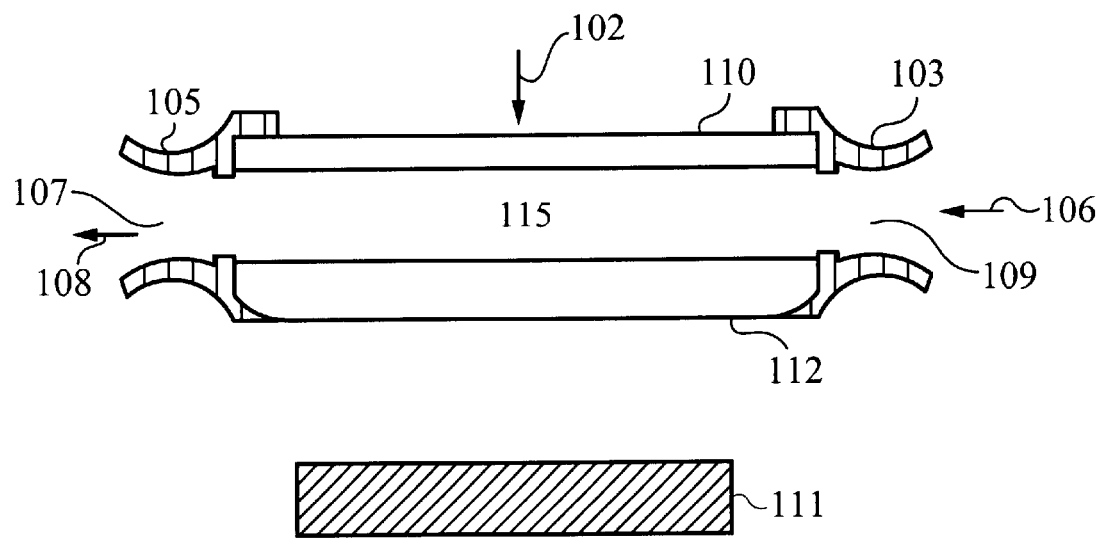

FIG. 1a is a top view of an optical window portion 100 of an application. The window portion 100 has a first lens 110 and a frame 101. The frame 101 is configured with apertures 107 and 109. Coupled to the apertures 107 and 109, are corresponding inlet and outlet sections 105 and 103, respectively, configured for coupling to a circulation mechanism (not shown). Now referring to FIG. 1b, the window portion 100 has a second lens 112 that is secured with the first lens 110 through the frame 101. The first lens 110 and the second lens 112 form the boundaries of a medium cavity 115. In use, a temperature modulating medium is channeled through the medium cavity 115 in a direction indicated by the arrows 106 and 108, wherein the temperature modulating medium flows through the medium cavity 115 and through the apertures 107 and 109. The window section 100 is placed proximal to a working surface 111 such that heat is transferred between the lens 112 and the working surface 111 while a laser beam 102 is directed to the working surface 111 through the window section 100.

Figure 2A:
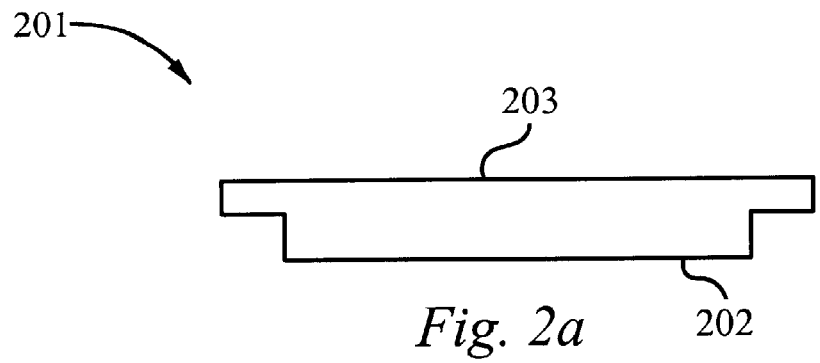
FIGS. 2a–d illustrate several lens configurations utilized in the applicator of the instant invention.
Figure 2B:
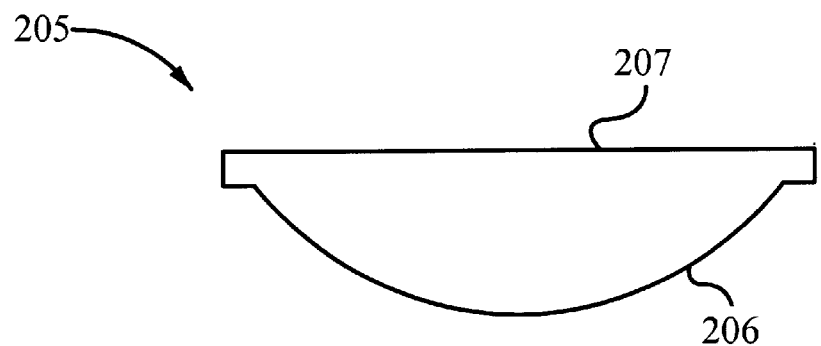
Figure 2C:
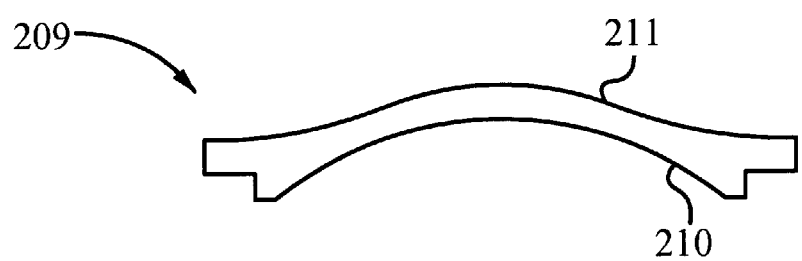
Figure 2D:
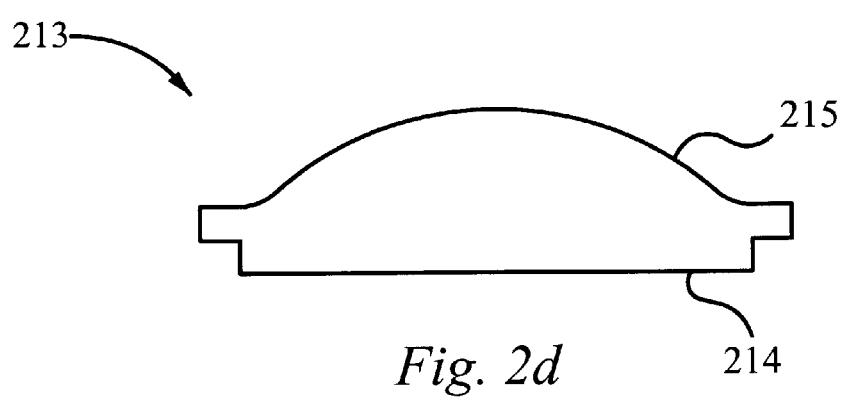

FIGS. 2a–d illustrate several lens configurations utilized in the applicator of the instant invention. The lens configurations described below are utilized as an upper lens 110, as a lower lens 112, as both the upper 110 and the lower lens 112 or alternatively as a focusing lens positioned between the upper 110 and the lower lens 112. In FIG. 2a the inner surface 203 and the outer surface 202 of the lens 201 are flat. In FIG. 2b, the inner surface 207 of the lens 205 is flat and the outer surface 206 of the lens 205 is curved or contoured. In FIG. 2c, the top surface 211 of the lens 209 is curved or contoured and the outer surface 210 of the lens 209 is also curved or contoured, in a complementary fashion. In FIG. 2d, the inner surface 215 of the lens 213 is curved or contoured and the outer surface 214 of the lens 213 is flat. FIGS. 2a–d are intended to be exemplary only. The optical surfaces of the lenses used in the instant invention can have any number of shapes and sizes depending on the intended application. The lenses are made from any suitable material which is substantially transparent to the radiation being used. Preferably, the lense used in contact with the work surface in the applicator of the instant invention is made from sapphire. The other lenses are preferably made from a material with lower heat conducting ability such as glass.

Figure 3A:
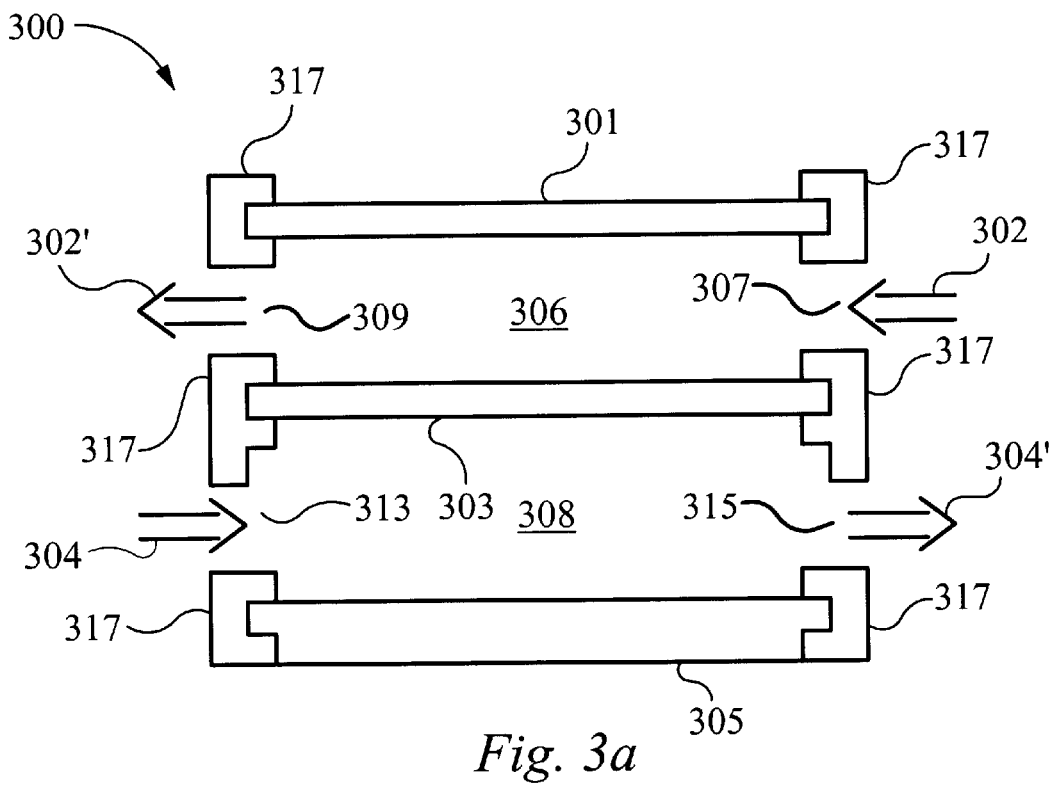
FIG. 3a is a schematic representation of a temperature modulating medium being channeled through the medium cavity and through the insulating region of an applicator.

FIG. 3a is a schematic representation of an applicator 300 configured to have a first temperature modulating medium channeled through the medium cavity 308. The medium cavity 308 is formed by an a first outer lens 305 and an inner lens 303. The applicator 300 is configured to have a second temperature modulating medium channel through an insulating region 306 formed by de a second outer lens 301 and the an inner lens 303. The lenses 301, 303 and 305 are secured together by the frame support 317 which preferably holds the lenses 301, 303 and 305 at predetermined distances from each other. In use, the first medium is channeled through the cavity 308 and through the apertures 313 and 315 as indicated by the arrows 304 and 304'. The second medium is channeled through the insulating region 306 and through the apertures 307 and 309 as indicated by the arrows 302 and 302'. The first temperature modulating medium and the second temperature modulating medium are liquids, gases or combination thereof. The first and second temperature modulating medium are the same medium or are different mediums. The applicator 300 is configured to channel the first and the second temperature modulating mediums in the same direction or in opposite directions, as shown. The first temperature modulating medium is channeled through the cavity 308 to modulate the temperature of the first outer lens 305, which is in turn used to modulate the temperature of a working surface. The second temperature modulating medium is channeled through the insulating region 306 to modulate the temperature of the second outer lens 301 and reduce fogging of the lens 301.

Figure 3B:
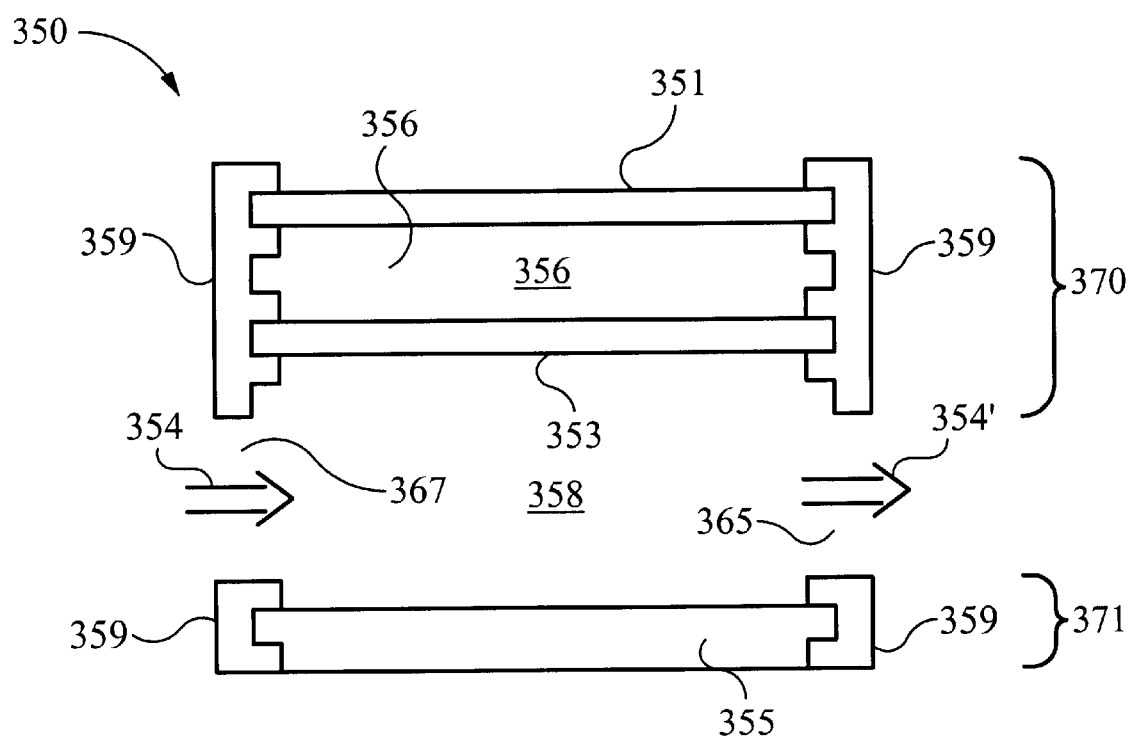
FIG. 3b is a schematic representation of a temperature modulating medium being channeled through the medium cavity of an applicator with a vacuum insulating region in accordance with the preferred embodiment of the instant invention.

FIG. 3b is a schematic representation of an applicator 350 configured to channel a temperature modulating medium through the medium cavity 358 and though the apertures 365 and 367, as indicated by the arrows 354 and 354'. A first lens sections 370 and a second lens section 371 form boundaries of a medium cavity 358. The first lens section 370 and the second lens section 371 are held together through a frame structure 359. The first lens section 355 has an outer lens 351 and an inner lens 353 which form boundaries of an insulating region 356. The insulating region 356 is preferably under vacuum in order to reduce the transfer of heat between the outer lens 351 and the temperature modulating medium channeled through the cavity 358, as described previously. In the case where the insulating region 356 is filled with dry gas, the inner walls of the frame structure 359 preferably contain a dessicating material known to absorb water such as a molecular sieve. The second lens section 371 comprises a second outer lens for contacting and cooling a working surface, as described in detail above.

Figure 3C:
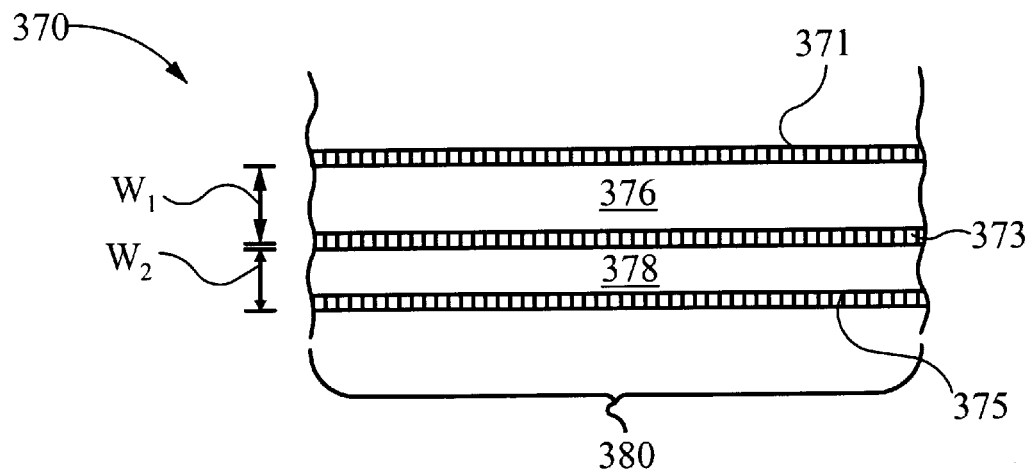
FIG. 3c illustrates a lens configuration according to a preferred embodiment of the instant invention.

FIG. 3c, illustrates a lens configuration 370 according to a preferred embodiment of the instant invention. The first outer lens 371 and the inner lens 373 are substantially parallel and form the boundaries of a vacuum or dry gas insulating region 376. The lenses 371 and 373 are preferably separated by an average distance $W_1$ in a range of 0.1 to 1.0 cm. The inner lens 373 and the second outer lens 375 form the boundaries of a medium cavity 378, through which a cooled liquid medium is channeled. The inner lens 373 and the second outer lens 375 are preferably separated by a distance $W_2$ in a range of 0.05 to 0.5 cm. Preferably, the volume of the insulating region 376 is more than twice the volume in the medium cavity 378. The optical area of the second outer lens 375 is preferably in a range of 1.0 to 50 $cm^2$ and is rounded or curved.

Figure 4A:
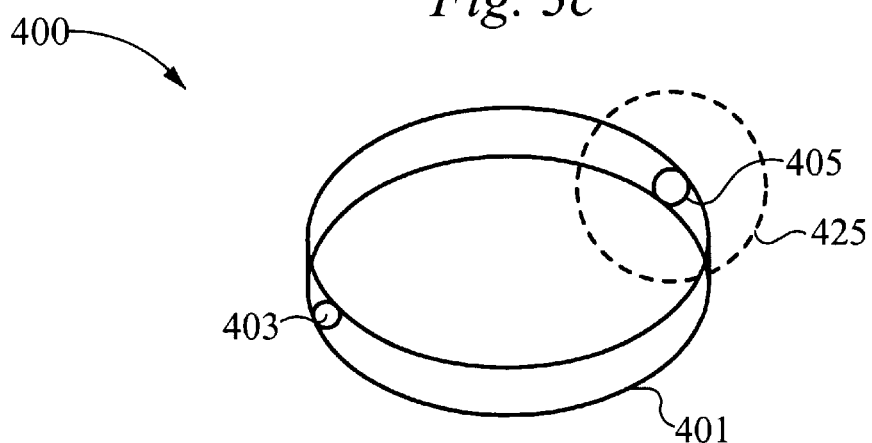
FIG. 4a illustrates a frame structure with an inlet aperture and an outlet aperture in accordance with the instant invention.
Figure 4B:
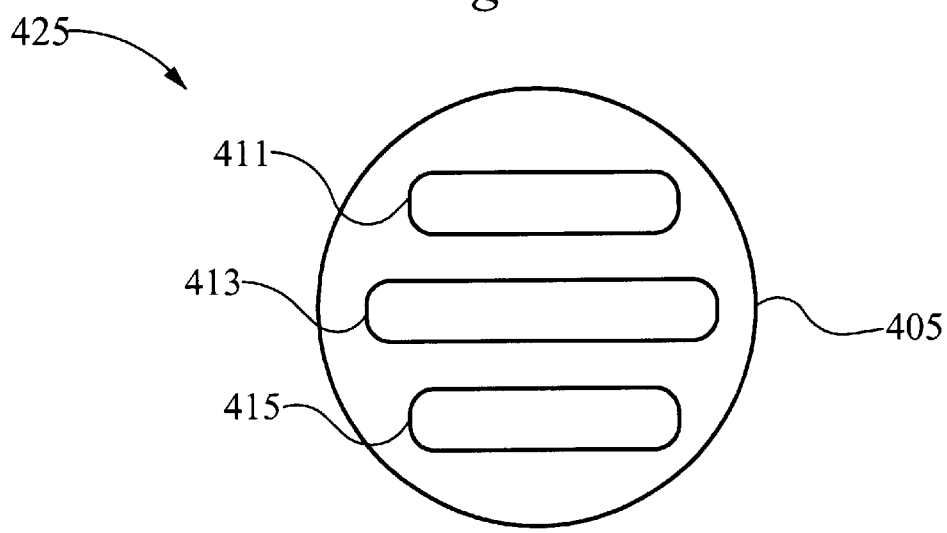
FIG. 4b illustrates an enlarged perspective of a fenestrated aperture in accordance with an embodiment of the instant invention.

Now referring to FIGS. 4a–b, the lenses are preferably held together by the frame structure 401 which includes a first aperture 403 and a second aperture 405. FIG. 4b shows an enlarged view 425 of the aperture 405. According to a preferred embodiment, the aperture 405 is fenestrated with a plurality of openings 411, 413 and 415 to help control the flow of the temperature modulating medium through the medium cavity.

Figure 5:
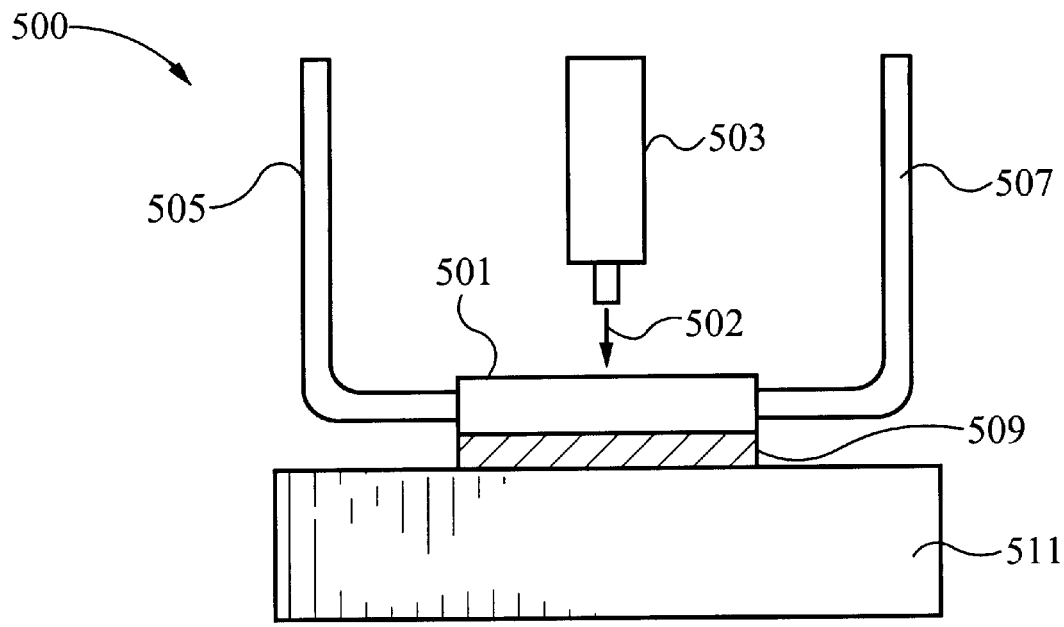
FIG. 5 shows a schematic representation of a laser applicator modulating the temperature of a working surface through a contact medium.

Now referring to FIG. 5, in use an applicator 501 is placed proximal to a working surface or target tissue 511. A cooling medium is circulated through an applicator 501. The applicator 501 is configured with a medium cavity and an insulating region as previously described. The temperature modulating medium is circulated through the medium cavity flowing through an inlet section 505 and an outlet section 507. A laser source 503 produces a laser beam 502 that is directed to the applicator and the exposed working surface 511 through the applicator 501. The applicator 501 is placed in direct contact with the working surface 511 or alternatively a suitable contact medium 509 is placed between the applicator 501 and the working surface 511 to facilitate the transfer of radiation to the working surface 511, the transfer of heat between the applicator 501 and the working surface 511 and/or to reduce friction between the applicator 501 and the working surface 511 as pressure is applied or as the applicator is moved from one position to another. Suitable contact mediums include dyes, gels, oil and combinations thereof.

Figure 6A:
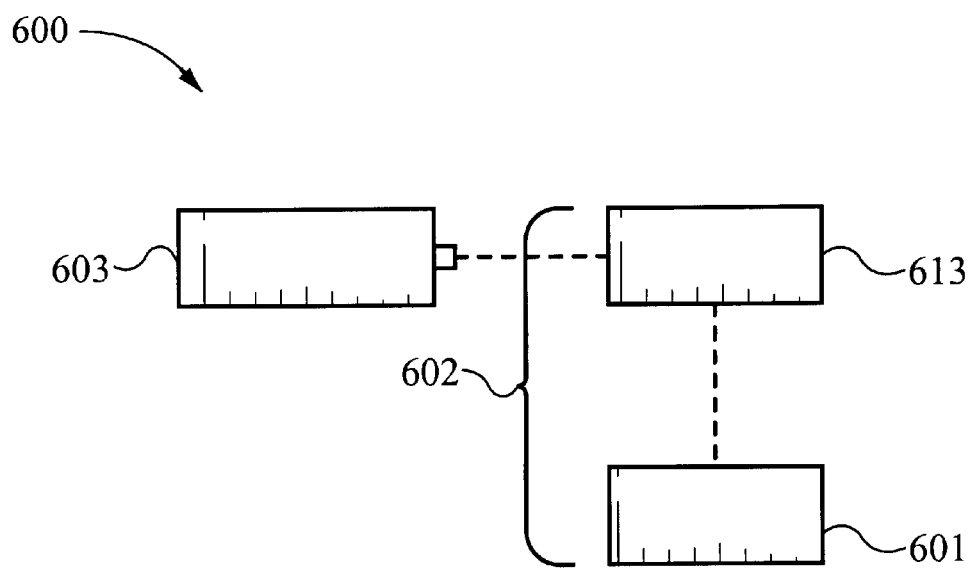
FIG. 6a is a schematic representation of an optical configuration having an applicator optical window and focusing optics for directing laser radiation to a target tissue.

Now referring to FIG. 6a, in the system 600 of the instant invention, a laser applicator 601 is configured with a medium cavity and an insulating region, as herein described. The applicator 600 is coupled to a laser source 603 through any suitable optics system 613. According to one embodiment, the laser applicator is coupled to the optics system 613 through a laser delivery housing.

Figure 6B:
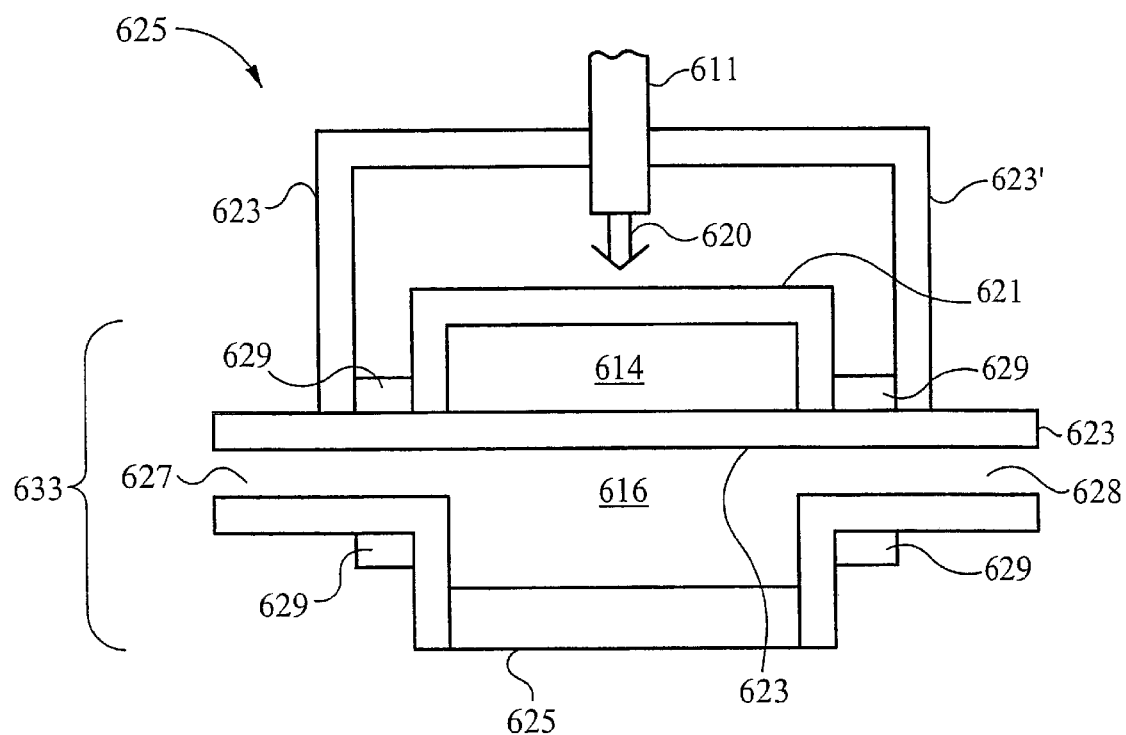
FIG. 6b shows an optical fiber coupled to the optical window of an applicator in accordance with the current invention.

FIG. 6b illustrates an applicator 625 configured with an optics system 613, as described with reference to FIG. 6a. The applicator 625 is configured with an optical fiber 611 coupled to an optical window 627 of the applicator 625 through support structures 623 and 623'. The applicator 625 has a vacuum insulating region 614 and a medium cavity 616. The lenses 621, 623 and 625 including a first outer lens 621, an inner lens 623 and a second outer lens, are secured through a suitable frame structure 629, similar to those previously described. In use, the optical fiber 611 delivers laser radiation from the laser source 603 (FIG. 6a) to the first outer lens 621. The laser radiation passes through the vacuum insulating region 614, the inner lens 623, a cooling medium circulating through the cavity 616 and through the second outer lens 625 onto the target tissue (not shown). The cooling medium is preferably a cooled liquid medium that is approximately 50% water and 50% ethylene glycol recirculated through the apertures 627 and 628. Preferably, the cooled liquid medium is recirculated through the medium cavity 616 by a circulation mechanism with a pump unit and a refrigerator unit (not shown). The refrigerator unit preferably cools the liquid medium to a temperature between −10 to +10 degrees centigrade before recirculating the liquid medium through the medium cavity 616 of the applicator 625.

Figure 6C:
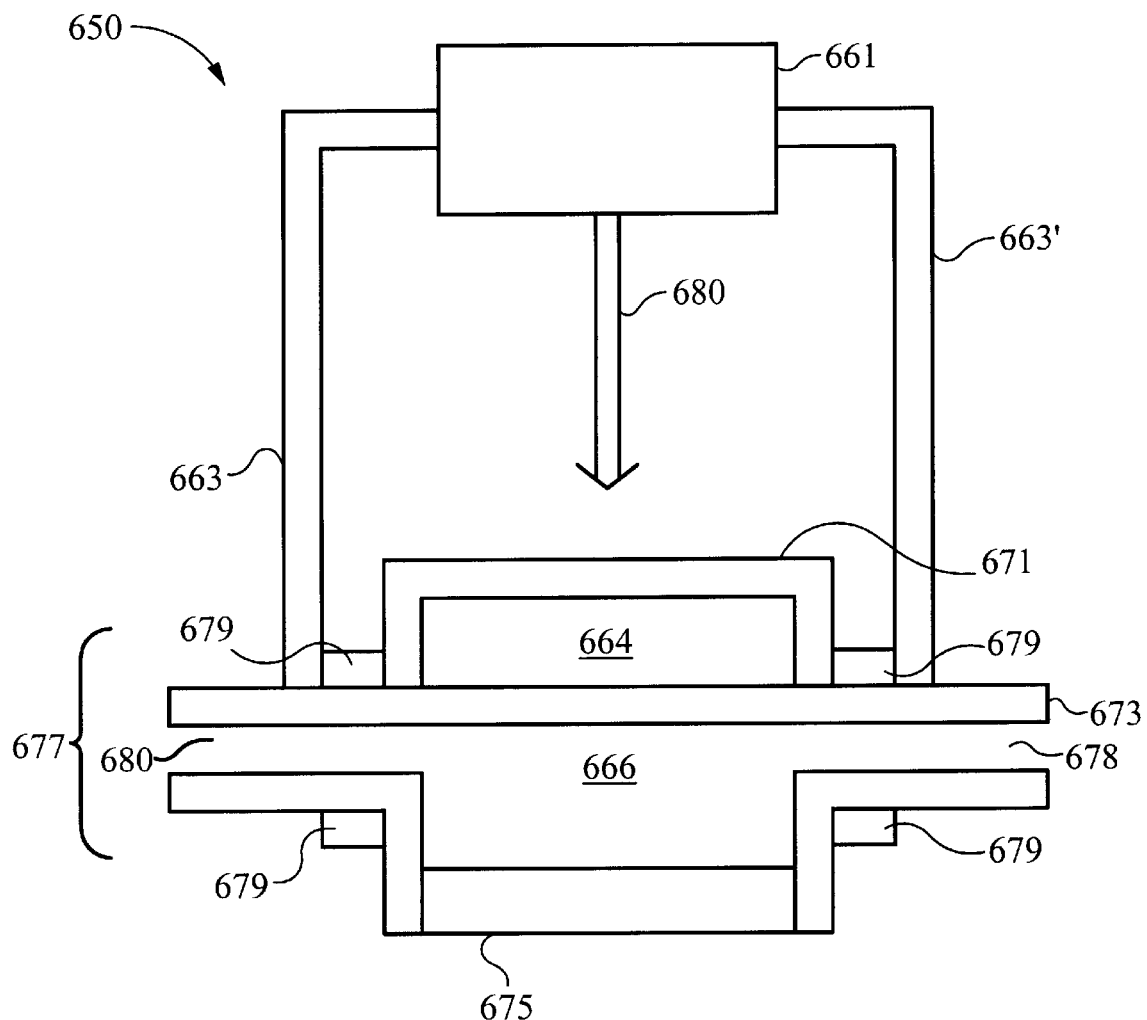
FIG. 6c shows a mirror coupled to the optical window of an applicator in accordance with an alternative embodiment of the instant invention.

FIG. 6c illustrates an applicator 650 to be used with an optics system 613 (FIG. 6A) in accordance with an alternative embodiment of the instant invention. The applicator 650 is configured with a mirror 661 coupled to an optical window 677 through the support structures 663 and 663'. The applicator 650 is configured with a vacuum insulating region 664 and a medium cavity 666. The lenses 671, 673 and 675, including a first outer lens 621, an inner lens 623 and a second outer lens, are secured with a suitable frame structure, similar to those previously described. In use, the mirror 661, delivers laser radiation 680 from the laser source 603 (FIG. 6A) to the first outer lens 671. The laser radiation 680 passes through the vacuum insulating region 664, the inner lens 673, a cooling medium circulating through the cavity 666 and through the second outer lens 675 onto the target tissue (not shown). It will be clear to one skilled in the art that the optics system 613 may include any number of other optical elements including focusing lens.

Figure 7A:
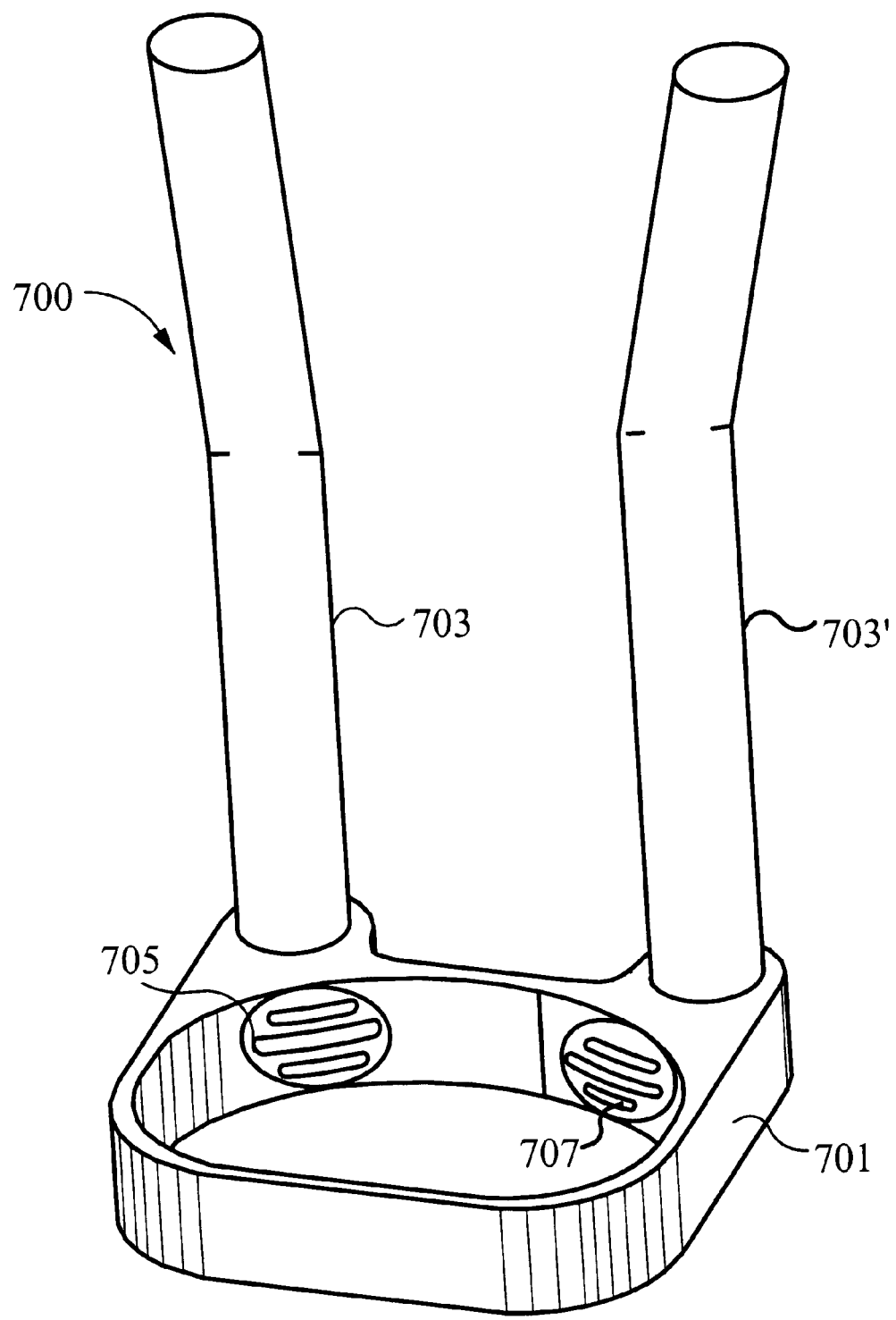
FIG. 7a shows a frame structure with rigid tubular inlet and outlet sections in accordance with the current invention.
Figure 7B:
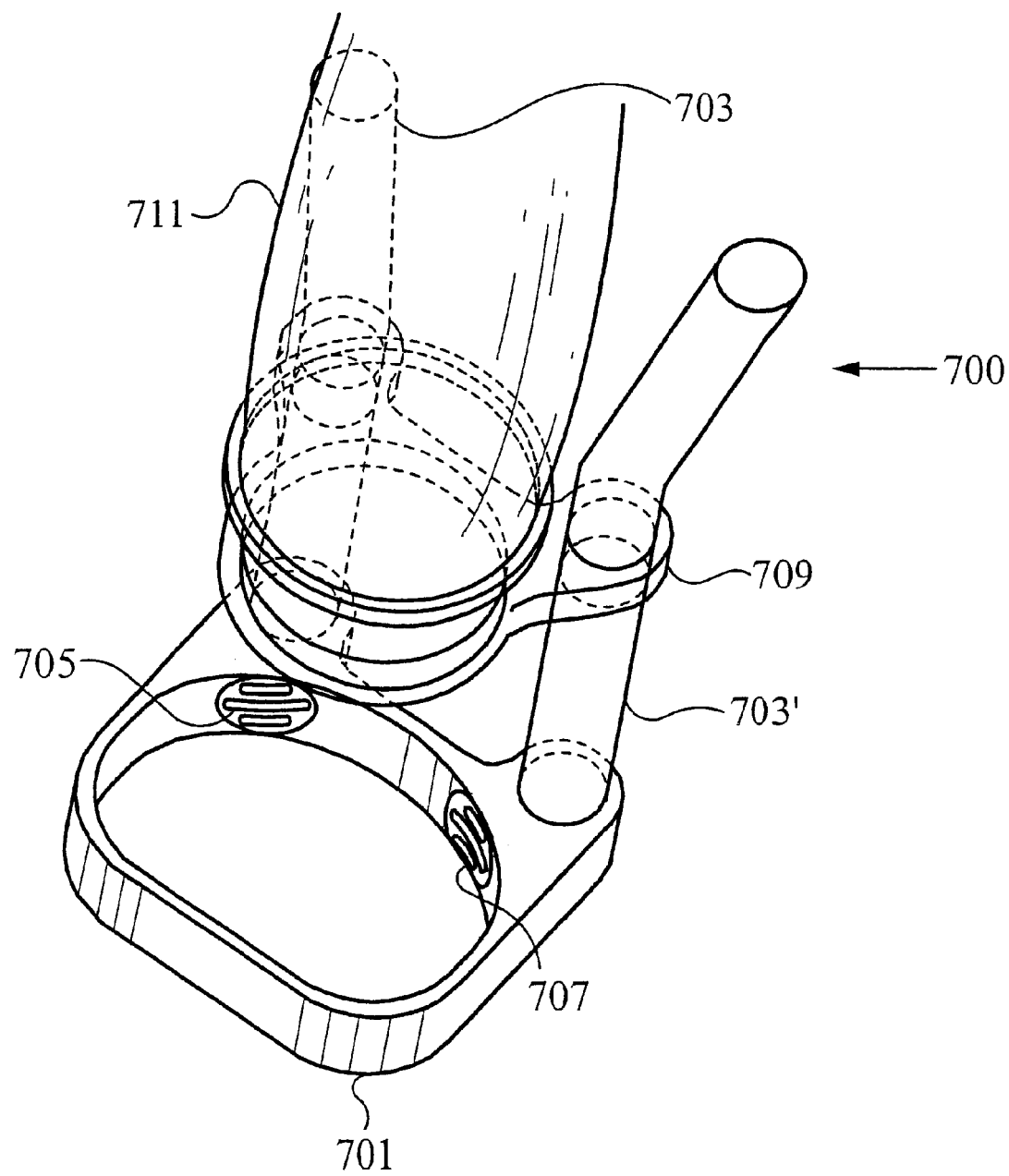
FIG. 7b shows the frame structure shown in FIG. 7a coupled to a laser housing through a bracket structure in accordance with an embodiment of the instant invention.

FIG. 7a shows a frame configuration 700 with a frame body 701 and rigid tubular inlet 703 and outlet 703' sections. The inlet 703 and outlet 703' sections are coupled to apertures 705 and 707 which are preferably fenestrated. FIG. 7b shows the frame configuration 700, such as shown in FIG. 7a, coupled to a laser delivery housing 711 through a bracket structure 709 that secures the frame configuration 700 to the laser delivery housing 711. Preferably, the bracket structure 709 secures the laser delivery housing 711 to the frame configuration 700 through the inlet 703 and outlet 703' sections. The laser delivery housing 711 serves as a handle while exposing a working surface to laser radiation and may also house optics, electronic or shutter mechanisms for controlling the laser source and the exposure levels of the laser.

Figure 8A:
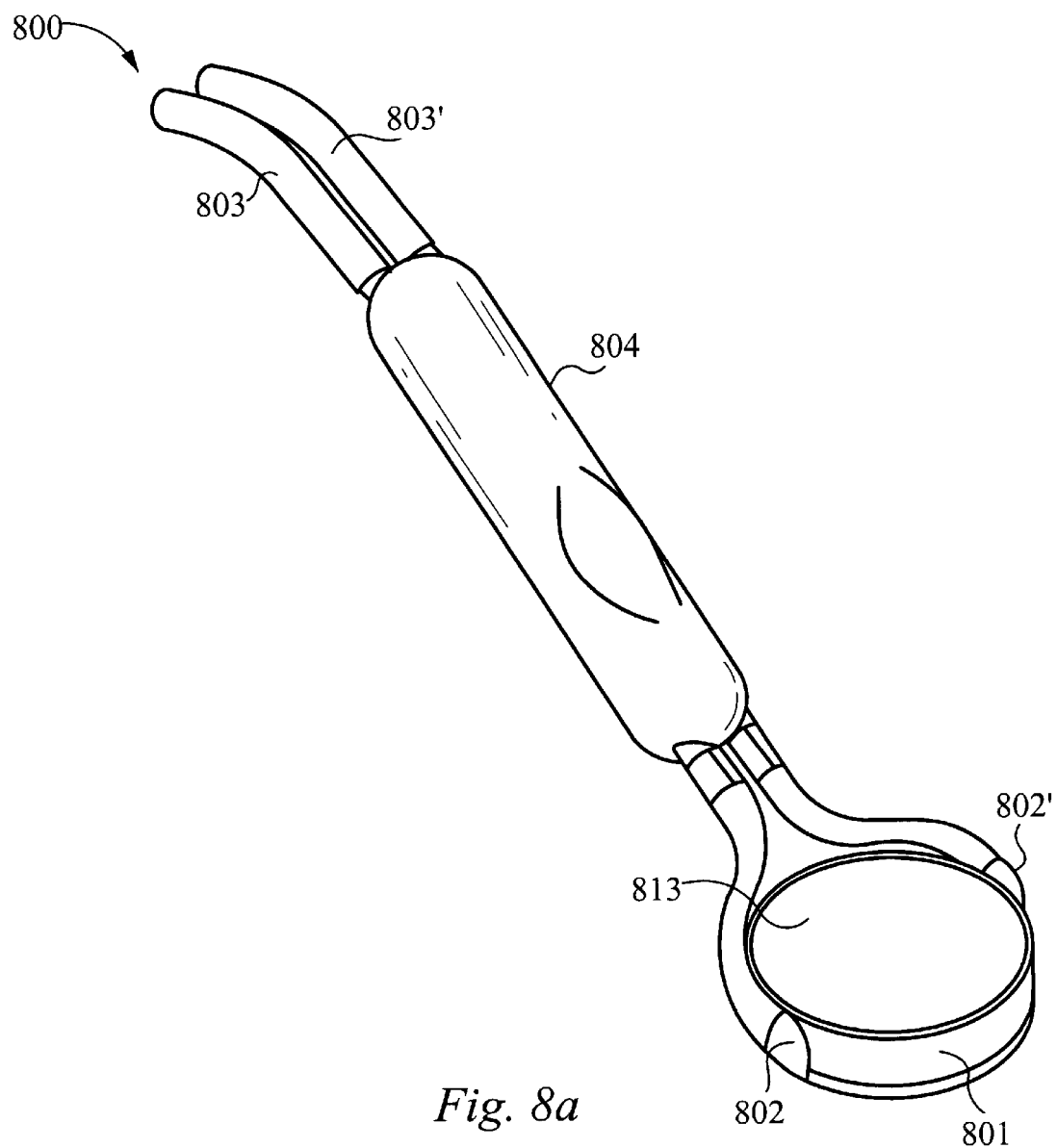
FIG. 8a shows a hand-held applicator in accordance with the instant invention.

FIG. 8a shows a hand-held laser applicator 800 with an optical window 813 having a vacuum insulating region and medium cavity as previously described. The optical window 813 is secured to the handle section 804 through inlet 802 and outlet 802' structures. The inlet 802 and outlet 802' structures are coupled to corresponding inlet 803 and outlet 803' circulation tubes that preferably pass through the handle section 804 and are configured to be coupled to a circulation mechanism.

Figure 8B:
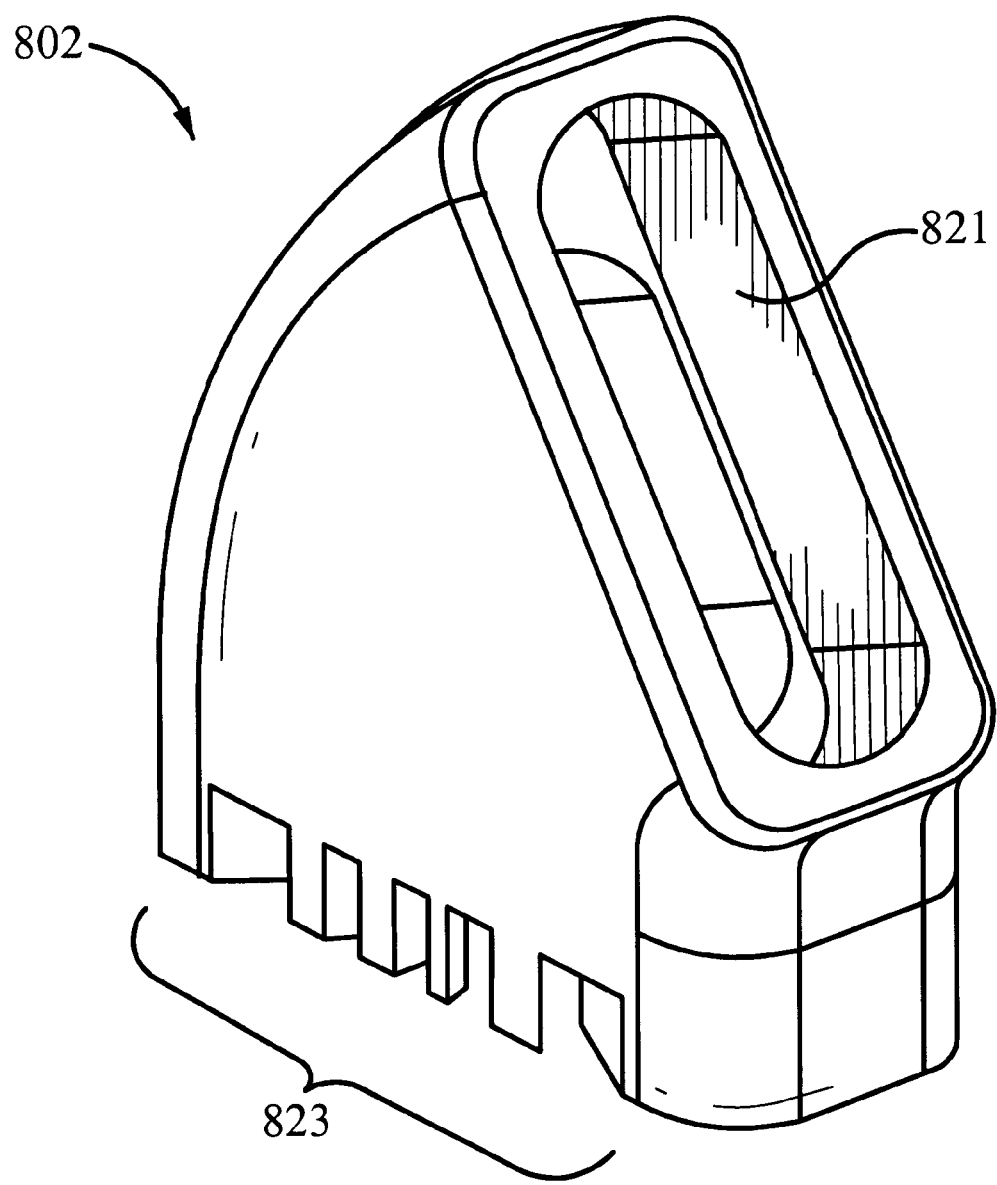

FIG. 8b shows an enlarged perspective view of the section 802. The section 802 has an aperture 821 through which a cooling medium is channeled into the medium cavity. The bottom portion 823 of the section 802 has a plurality of slotted aperture features that connect through the aperture 821. The slotted aperture features control the flow of the cooling medium and help prevent air from trapping within the optical window 813 of the applicator 800 during system startups.

Figure 8C:
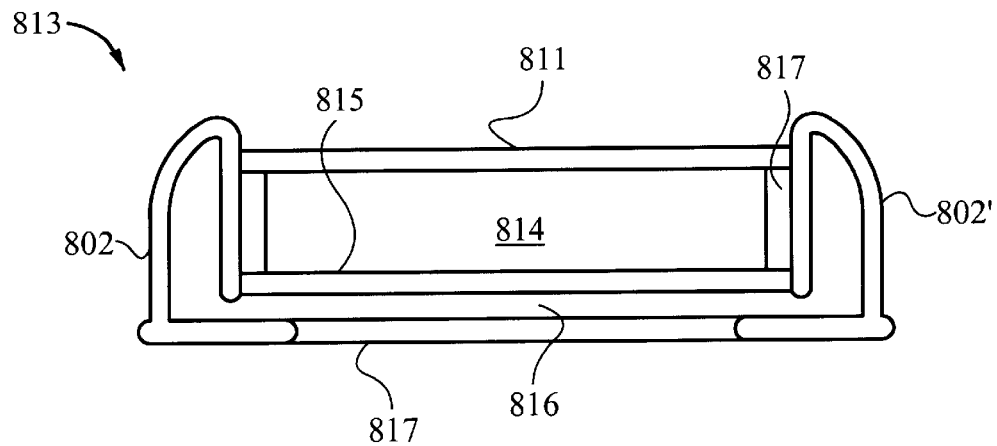

FIG. 8c shows a cross-sectional representation of the optical window 813 of the applicator shown in FIG. 8a. The optical window 813 comprises a first outer lens 811, an inner lens 815 and a second outer lens 817. The optical window 813 also has an inlet 802 and outlet 802' section through which a cooled liquid medium enters and exits a medium cavity 816. The first outer lens 811 and the inner lens 815 form the boundaries of a vacuum or dry gas insulating region 814 and are preferably made of glass or other low heat conducting transparent material. In the case of an insulating gas in the insulating region 814, the insulating walls or seals 817 of the insulating region 814 are made of a dessicating material. The volume of the insulating region 814 is preferably greater than the volume of the medium cavity 816 as schematically shown.

Figure 9:
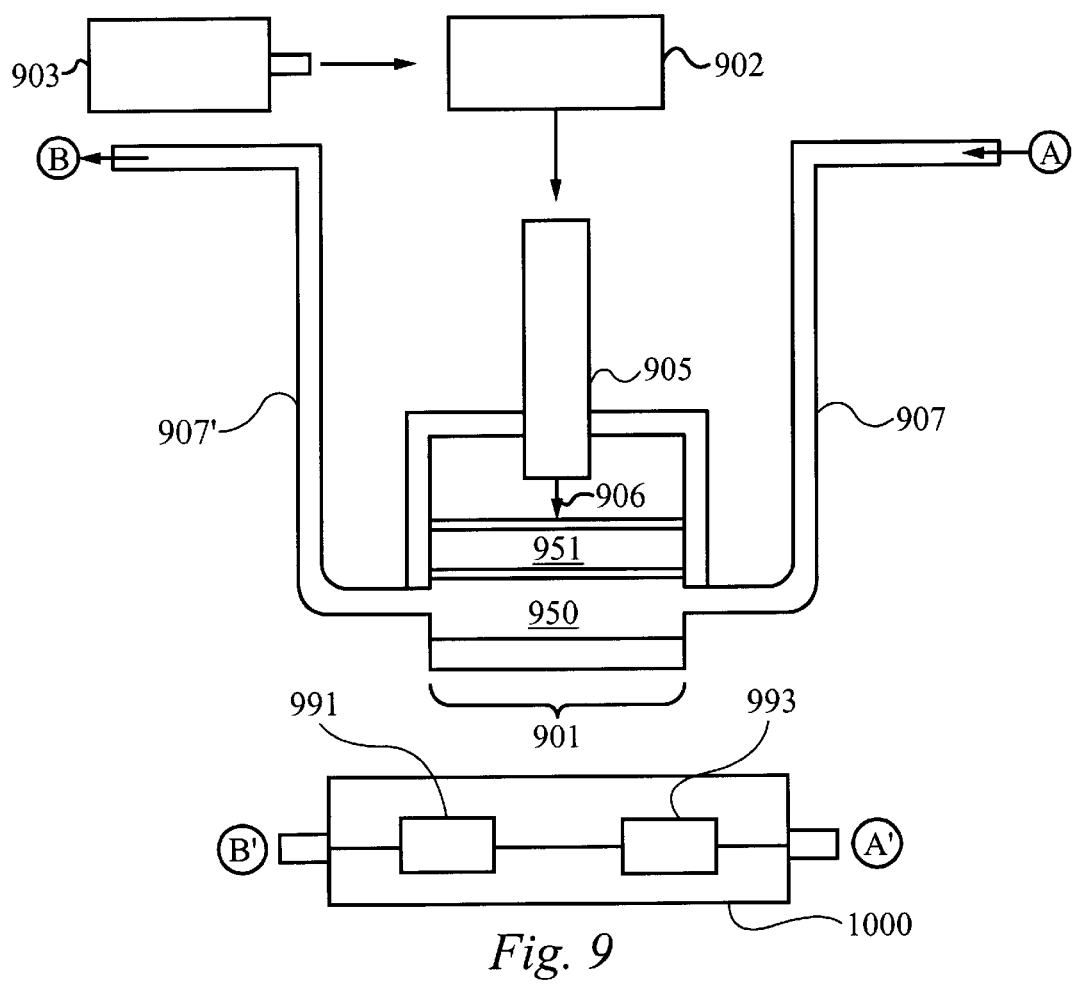
FIG. 9 shows a schematic representation of a laser system with an applicator in accordance with the current invention.

FIG. 9 illustrates a laser system 900 in accordance with the instant invention. In the laser system 900 of the instant invention, a laser source 903 is preferably a pulsed laser source for providing pulsed laser radiation with a wavelength in a range of 400 to 11,000 nm. The laser source 903 is coupled to suitable optics 902 for focusing and directing laser radiation to a laser delivery structure 905. The laser delivery structure 905 is preferably a hand-held housing that houses a portion of the optics 902. The laser beam 906 is directed onto the optical window of the applicator 901 and onto the target tissue, wherein the optical window comprises a first outer lens, an inner lens and a second outer lens such as described above. The applicator 901 is placed in communication with the target tissue (not shown), preferably to remove heat from the target tissue while simultaneously exposing the target tissue to the laser radiation. The target tissue is cooled by virtue of a cooled liquid medium that is circulated through the medium cavity 950. The applicator 901 is configured with inlet 907 and outlet tubes 907' coupled to corresponding outlet and inlets of a circulating mechanism 1000. The circulating mechanism 1000 preferably has a pump unit 991 for urging cooled liquid medium through the medium cavity 950 and a refrigerator unit 993 for maintaining the liquid medium at temperatures between −10 to +10 degrees centigrade before recirculating the liquid medium through medium cavity 950 of the applicator 901. The vacuum insulating region 951 reduces the rate of condensation on the optical window of the applicator 901 while cooling the target tissue.

A laser applicator with an insulating region, as described above, minimizes the fogging on the optical window that is typically observed in prior art laser applicators. The laser applicator of the current invention provides physicians with a low cost and low maintenance method to modulate the temperature of dermis while simultaneously exposing the dermis to a laser source. The laser applicator enhances the physician's visibility of tissue and reduces laser scattering which is typically caused by fogging on the laser applicators of the prior art. The laser applicator of the present invention is adaptable to a wide variety of laser sources and medium circulating mechanisms. Further, the laser applicator of the instant invention is compatible with a wide variety of medical laser procedures and is especially well suited for use during laser assisted hair removal and treatment of Port Wine Stains.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiment chosen for illustration without departing from the spirit and scope of the invention. Specifically, it will be apparent to one of ordinary skill in the art that any number of circulating and recirculating configurations may be utilized with the applicator of the instant invention.

What is claimed is:

1. An apparatus for modulating temperature of a working surface while treating the working surface with a laser source, comprising:
   a. a first lens section comprising an outer lens and an inner lens, wherein the outer lens and the inner lens are spaced to form an insulating region;
   b. a second lens section positioned adjacent to the first lens section; and
   c. a frame configured for securing the first and second lens sections together to form a medium cavity for channeling a temperature modulating medium between the inner lens of the first lens section and the second lens section.

2. The apparatus of claim 1, wherein the insulating region is configured to channel a second temperature modulating medium.

3. The apparatus of claim 1, wherein the insulating region is a vacuum region.

4. The apparatus of claim 1, wherein the frame comprises a first and a second aperture through which the temperature modulating medium enters and exits the medium cavity.

5. The apparatus of claim 4, wherein at least one of the first and second apertures is fenestrated.

6. The apparatus of claim 4, wherein the first aperture is coupled to an inlet section and the second aperture is coupled to an outlet section, wherein the inlet section and the outlet section are configured to couple to a circulating system, for recirculating the temperature modulating medium.

7. The apparatus of claim 6, further comprising a bracket for securably coupling to a laser delivery housing, such that a laser beam delivered from the housing is securably positioned to pass through the first lens section, the second lens section and the temperature modulating medium.

8. The apparatus of claim 7, wherein the inlet and outlet sections are rigid tubular sections.

9. The apparatus of claim 8, wherein the rigid tubular sections are hingably coupled to the frame.

10. The apparatus of claim 8, wherein the bracket is configured to couple to the laser delivery housing through the rigid tubular sections.

11. The apparatus of claim 1, wherein the outer lens and the inner lens of the first lens section are spaced apart by an average distance of 0.1 to 1.0 cm.

12. The apparatus of clam 1, wherein the first lens section and the second lens section are separated by an average distance of 0.05 to 0.5 cm.

13. The apparatus of claim 1, wherein the second lens section has an optical surface area between 1.0 to 50 $cm^2$.

14. The apparatus of claim 1, wherein the second lens section comprises a contoured lens.

15. The apparatus of claim 1, wherein at least one of the first and second lens sections comprises a sapphire lens.

16. The apparatus of claim 1, wherein the working surface is dermis and the apparatus is configured to remove hair.

17. The apparatus of claim 1, wherein the working surface is dermis and the apparatus is configured to treat cutaneous vascular lesions.

18. A system for treating a target tissue with laser radiation, the system comprising an optical configuration for coupling to a laser source and transferring the laser radiation from the laser source to the target tissue, the optical configuration comprising a temperature modulator, wherein the temperature modulator comprises:
   a. a first lens section with an outside surface and an inside surface wherein the outside surface and the inside surface are separated by an insulating interface;
   b. a second lens section with an outside surface and an inside surface; and
   c. a frame configured for securing the first and second lens section together to form a medium cavity for channeling a temperature modulating medium between the interface of the first lens section and the inside surface of the second lens section: and
   d. a bracket for adjusting a position of the temperature modulator relative to an optical element.

19. The system of claim 18, wherein the insulating interface comprises a vacuum region.

20. The system of claim 18, wherein the optical element is selected from the group consisting of a lens and an optical fiber.

21. The system of claim 20, further comprising a delivery housing for housing the optical element.

22. The system of claim 18, wherein the temperature modulator comprises a first and a second aperture coupled to the medium cavity.

23. The system of claim 22, farther comprising a circulation mechanism for circulating the temperature modulating medium through the medium cavity and through the first and second apertures.

24. The system of claim 23, wherein the circulation mechanism is configured for circulating a liquid through the medium cavity and through the first and second apertures.

25. The system of claim 24, wherein at least one of the first and second apertures is fenestrated to control the flow of the temperature modulating medium through the medium cavity.

26. The system of claim 18, wherein at least one of the first and second lens sections comprises a sapphire lens.

27. A method of treating dermis comprising:
   a. exposing the dermis to radiation through a temperature modulating applicator, wherein the temperature modulating applicator comprises:
      i. a first lens section comprising an outer lens and an inner lens separated by an insulating region; and
      ii. a second lens section, wherein the inner lens of the first lens section and the second lens section form boundaries of a medium cavity; and
   b. flowing a temperature modulating medium through the medium cavity to simultaneously regulate the temperature of the dermis while exposing the dermis to radiation.

28. The method of claim 27, further comprising flowing a second temperature modulating medium through the insulating region.

29. The method of claim 27, wherein the insulating region is under vacuum.

30. The method of claim 27, wherein the temperature modulating medium is a liquid medium.

31. The method of claim 30, wherein the liquid medium is a mixture of water and ethylene glycol regulated to temperatures in the range of −10.0 to +10.0 degrees centigrade prior to flowing through the medium cavity.

32. The method of claim 27, wherein the second lens section is placed in contact with the dermis.

33. The method or claim 27, wherein a contact medium is placed between the dermis and the second lens section.

34. The method of claim 27, wherein the radiation is generated from a laser source.

35. The method of claim 34, wherein the laser source has a wavelength in the range of 400 to 11,000 nm.

36. The method of claim 34, wherein the laser source us a pulsed laser.

37. The method of claim 27, wherein exposing the dermis to radiation through a temperature modulating applicator removes hair follicles.

38. The method of claim 27, wherein exposing the dermis to radiation through a temperature modulating applicator reduces cutaneous vascular lesions.

39. A system for exposing dermis comprising:
   a. means for generating laser radiation with a predetermined pulsed sequence;
   b. means for directing the laser radiation to the dermis; and
   c. a temperature regulator comprising a cooling surface and an insulated surface, wherein the cooling surface is configured to cool the dermis, while simultaneously exposing the dermis to the laser radiation, and wherein the insulated surface and the cooling surface are separated by a vacuum region and a cooling region for channeling a temperature modulating medium between the vacuum region and the cooling surface.

40. The system of claim 39, further comprising a liquid circulation mechanism for recirculating a cooled liquid between the insulated surface and the cooling surface.

41. A system for exposing dermis comprising:
   a. a pulsed laser source for generating laser radiation;
   b. an optical configuration for directing the laser radiation to the dermis, the optical configuration having an applicator comprising:
      i. a first lens section with a first outside surface and a first inside surface wherein the outside surface and the inside surface are separated by an insulating interface;
      ii. a second lens section with a second outside surface and second inside surface;
      iii. a frame with a fenestrated inlet and a fenestrated outlet, the frame configured for securing the first and second lens sections together to form a medium cavity for channeling a temperature modulating medium between the interface of the first lens section and the inside surface of the second lens section; and
      iv. a circulation pump coupled to the fenestrated inlet and fenestrated outlet for circulating the temperature modulating medium through the medium cavity and through the inlet and outlet.

42. The system of claim 41, further comprising a refrigerator unit coupled to the circulation pump to cool the temperature modulating medium before circulating the temperature modulating medium through the medium cavity and through the fenestrated inlet and fenestrated outlet.

43. The system of claim 42, wherein the temperature modulating medium is liquid.

44. A method of making a laser applicator comprising:
   a. securing a first lens section and a second lens section together through a body section, wherein the first lens section and the second lens section are positioned adjacent to each other and form a cavity, wherein the first lens section comprises a thermo-pane structure; and
   b. coupling the cavity to an inlet and an outlet section configured to couple to a circulation mechanism for circulating a temperature regulating medium through the medium cavity.

* * * * *

UNITED STATES PATENT AND TRADEMARK OFFICE
CERTIFICATE OF CORRECTION

PATENT NO. : 6,770,069 B1
DATED : August 3, 2004
INVENTOR(S) : James L. Hobart, Daniel K. Negus It is certified that error appears in the above-identified patent and that said Letters Patent is hereby corrected as shown below:

Title page,
Item [56], References Cited, OTHER PUBLICATIONS, please replace "N. Douglas Gossman" with -- M. Douglas Gossman --.

Column 10,
Line 21, replace ":" with -- ; --.

Signed and Sealed this

Twenty-first Day of September, 2004

JON W. DUDAS
*Director of the United States Patent and Trademark Office*